(12) United States Patent
Startare et al.

(10) Patent No.: US 9,700,694 B2
(45) Date of Patent: Jul. 11, 2017

(54) PATIENT INTERFACE DEVICE INCLUDING A DYNAMIC SELF ADJUSTMENT MECHANISM

(75) Inventors: Anthony Vincent Startare, Eindhoven (NL); Anthony Jon Bafile, Eindhoven (NL); Christopher Adam Cioccio, Eindhoven (NL); David Smith, Eindhoven (NL); Peter Chi Fai Ho, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 647 days.

(21) Appl. No.: 13/814,511

(22) PCT Filed: Aug. 4, 2011

(86) PCT No.: PCT/IB2011/053476
§ 371 (c)(1),
(2), (4) Date: Feb. 6, 2013

(87) PCT Pub. No.: WO2012/020359
PCT Pub. Date: Feb. 16, 2012

(65) Prior Publication Data
US 2013/0133664 A1      May 30, 2013

Related U.S. Application Data

(60) Provisional application No. 61/371,869, filed on Aug. 9, 2010.

(51) Int. Cl.
*A61M 16/06* (2006.01)

(52) U.S. Cl.
CPC ........ *A61M 16/06* (2013.01); *A61M 16/0611* (2014.02); *A61M 16/0638* (2014.02); *A61M 16/0666* (2013.01); *A61M 16/0644* (2014.02)

(58) Field of Classification Search
CPC .............. A61M 16/0683; A61M 16/06; A61M 16/0666; A61M 16/0661; A61M 16/0611;
(Continued)

(56) References Cited

U.S. PATENT DOCUMENTS

2005/0011522 A1\* 1/2005 Ho .................... A61M 16/0633
128/206.21
2006/0027237 A1 2/2006 Sleeper
(Continued)

FOREIGN PATENT DOCUMENTS

CN 101389369 A 3/2009
CN 101472637 A 7/2009
(Continued)

*Primary Examiner* — Lynne Anderson
*Assistant Examiner* — Elliot S Ruddie
(74) *Attorney, Agent, or Firm* — Michael W. Haas

(57) ABSTRACT

A patient interface device (8, 8') for delivering a flow of breathing gas to an airway of a patient includes a grooved adjustment mechanism (20, 58, 78) having a main body (22, 60) formed from an elastic material, the main body having an outer surface having a plurality of convolutions (80) provided therein. Each convolution including a groove (24, 62, 84), and each convolution has a stiffness associated therewith. The stiffnesses associated with the convolutions increase from a first side of the main body to a second side of the main body.

9 Claims, 12 Drawing Sheets

(58) Field of Classification Search
CPC .......... A61M 16/0633; A61M 16/0622; A61M 16/0638; A61M 16/0616; A61M 16/08; A61M 16/0816; A61M 2210/0618; Y10S 128/912
USPC ............ 128/204.18, 205.25, 206.21, 206.24, 128/206.27, 207.11, 204.23, 205.13, 128/206.11, 207.13, 207.18
See application file for complete search history.

(56) References Cited

U.S. PATENT DOCUMENTS

| | | |
|---|---|---|
| 2007/0044804 A1* | 3/2007 | Matula et al. ............ 128/206.21 |
| 2007/0221228 A1* | 9/2007 | Ho et al. .................. 128/206.24 |
| 2007/0277828 A1 | 12/2007 | Ho |
| 2008/0060653 A1 | 3/2008 | Hallett |
| 2008/0196727 A1 | 8/2008 | Ho |
| 2008/0245369 A1 | 10/2008 | Matula |
| 2008/0276938 A1 | 11/2008 | Jeppesen |
| 2009/0139526 A1* | 6/2009 | Melidis ................. A61M 16/06 128/206.26 |
| 2010/0065059 A1* | 3/2010 | Ho ........................... 128/206.24 |
| 2010/0163049 A1* | 7/2010 | Osier ..................... A61M 16/06 128/206.24 |

FOREIGN PATENT DOCUMENTS

| | | |
|---|---|---|
| DE | 10051897 C1 | 4/2003 |
| WO | WO0162326 A1 | 8/2001 |
| WO | WO2005123166 A1 | 12/2005 |
| WO | WO2007021777 A2 | 2/2007 |
| WO | WO2007143793 A1 | 12/2007 |
| WO | 2009108995 A1 | 9/2009 |

* cited by examiner

PATIENT INTERFACE DEVICE INCLUDING A DYNAMIC SELF ADJUSTMENT MECHANISM

CROSS-REFERENCE TO RELATED APPLICATIONS

This patent application claims the priority benefit under 35 U.S.C. §371 of international patent applications no. PCT/IB2011/053476, filed Aug. 4, 2011, which claims the priority benefit under 35 U.S.C. §119(e) of U.S. Provisional Application No. 61/371,869 filed on Aug. 9, 2010, the contents of which are herein incorporated by reference.

BACKGROUND OF THE INVENTION

1. Field of the Invention

The present invention relates to patient interface devices for transporting a gas to and/or from an airway of a user, and in particular, to a patient interface device including a dynamic self adjustment mechanism for adjusting, for example and without limitation, mask position and/or pressure.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

For such patient interface devices, a key engineering challenge is to balance patient comfort against mask stability, i.e., the patient interface device stays properly fitted on the user. This is particularly true in the case of treatment of OSA, where such patient interface devices are typically worn for an extended period of time. As a patient changes sleeping positions through the course of the night, masks tend to become dislodged, and the seal can be broken. A dislodged mask can be stabilized by increasing strapping force, but increased strapping force tends to reduce patient comfort. This design conflict is further complicated by the widely varying facial geometries that a given mask design needs to accommodate.

One area where facial geometries vary a great deal is the angle of the base of the nose (known as the nasolabial angle). As is known, this angle can range from ~58° to ~114° (Ave±1SD). This creates difficulty in providing a single patient interface design that fits a range of users. Another area where fit and comfort is often a concern is the bridge of the patient's nose, as many patient interface devices will apply a pressure to this area. If this pressure is not able to be managed effectively, either or both of a poor fit or patient discomfort will result, thereby limiting the effectiveness of the device.

SUMMARY OF THE INVENTION

Accordingly, it is an object of the present invention to provide a patient interface device that overcomes the shortcomings of conventional device. This object is achieved according to one embodiment of the present invention by providing, in one embodiment, a patient interface device for delivering a flow of breathing gas to an airway of a patient that includes a grooved adjustment mechanism having a main body formed from an elastic material. The main body has an outer surface having a plurality of convolutions provided therein. Each convolution includes a groove, and each convolution has a stiffness associated therewith. The stiffnesses associated with the convolutions increase from a first side of the main body to a second side of the main body.

In another embodiment, a method of adjusting a patient interface device structured to deliver a flow of breathing gas to an airway of a patient is provided that includes donning the patient interface device, wherein the patient interface device includes a grooved adjustment mechanism having a main body formed from an elastic material, the main body having an outer surface having a plurality of convolutions provided therein, each convolution including a groove, wherein each convolution has a stiffness associated therewith, wherein the stiffnesses associated with the convolutions increase from a first side of the main body to a second side of the main body, and applying a force to the patient interface device, wherein in response to the force, one or more of the convolutions are caused to collapse.

In still another embodiment, a patient interface device for delivering a flow of breathing gas to an airway of a patient is provided that includes a grooved adjustment mechanism having a main body formed from an elastic material, the main body having an outer surface having a first groove and a second groove provided therein, each of the first groove and the second groove extending laterally around at least a portion of the main body, the first groove having a first width, a first thickness and a first length, the second groove having a second width, a second thickness and a second length, wherein the first width is different than the second width, the first thickness is different than the second thickness and the first length is different than the second length.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
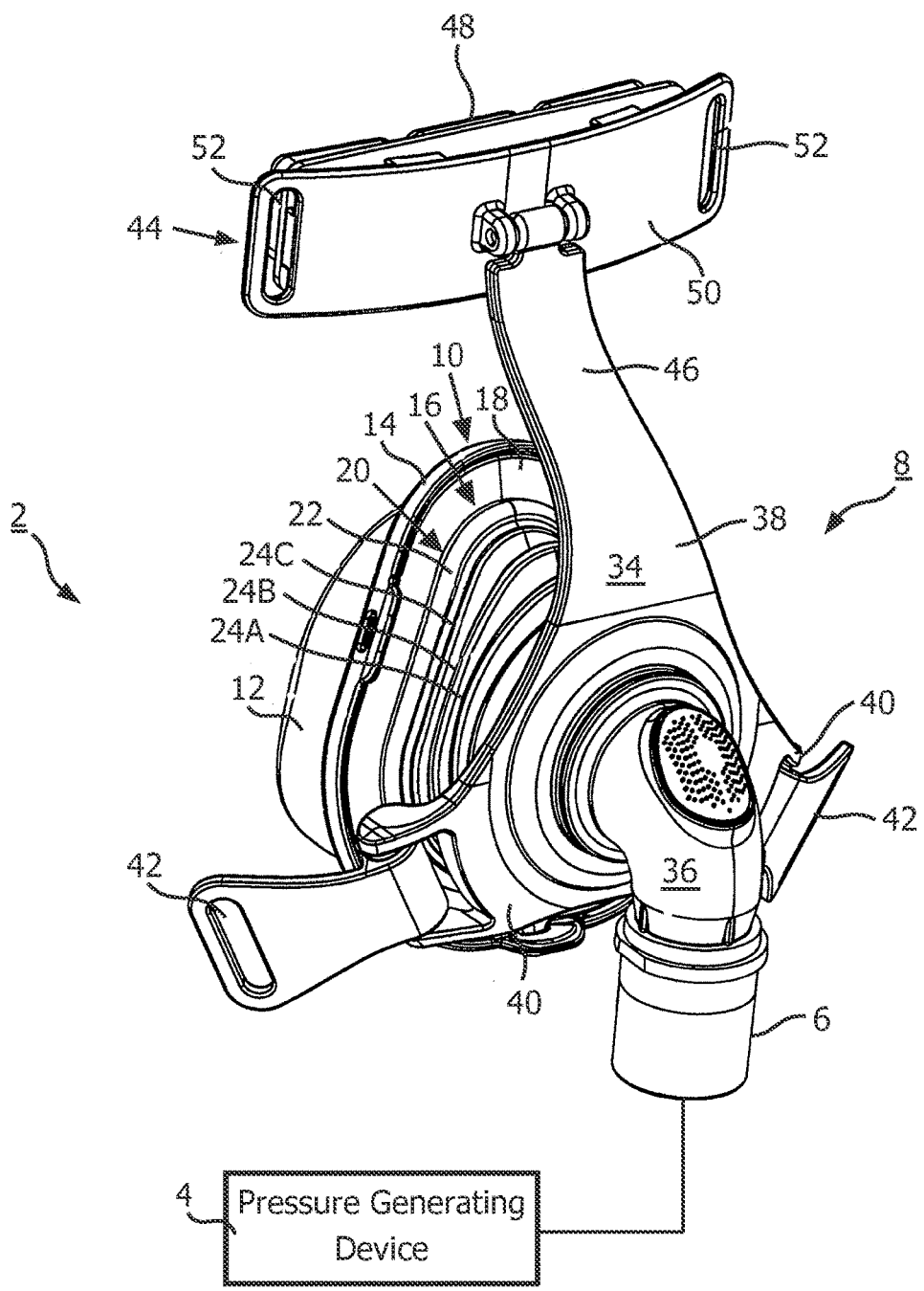
FIG. 1 is a schematic view of a system adapted to provide a regimen of respiratory therapy to a patient according to one exemplary embodiment of the present invention showing a perspective view of a patient interface device used in such a system.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the term "stiffness" shall mean the resistance of an elastic body to deformation by an applied force along a given degree of freedom, and shall be expresses as $k=P/\delta$, wherein k is stiffness, P is the force applied on the body, and $\delta$ is the displacement produced by the force P along the same degree of freedom.

Figure 2:
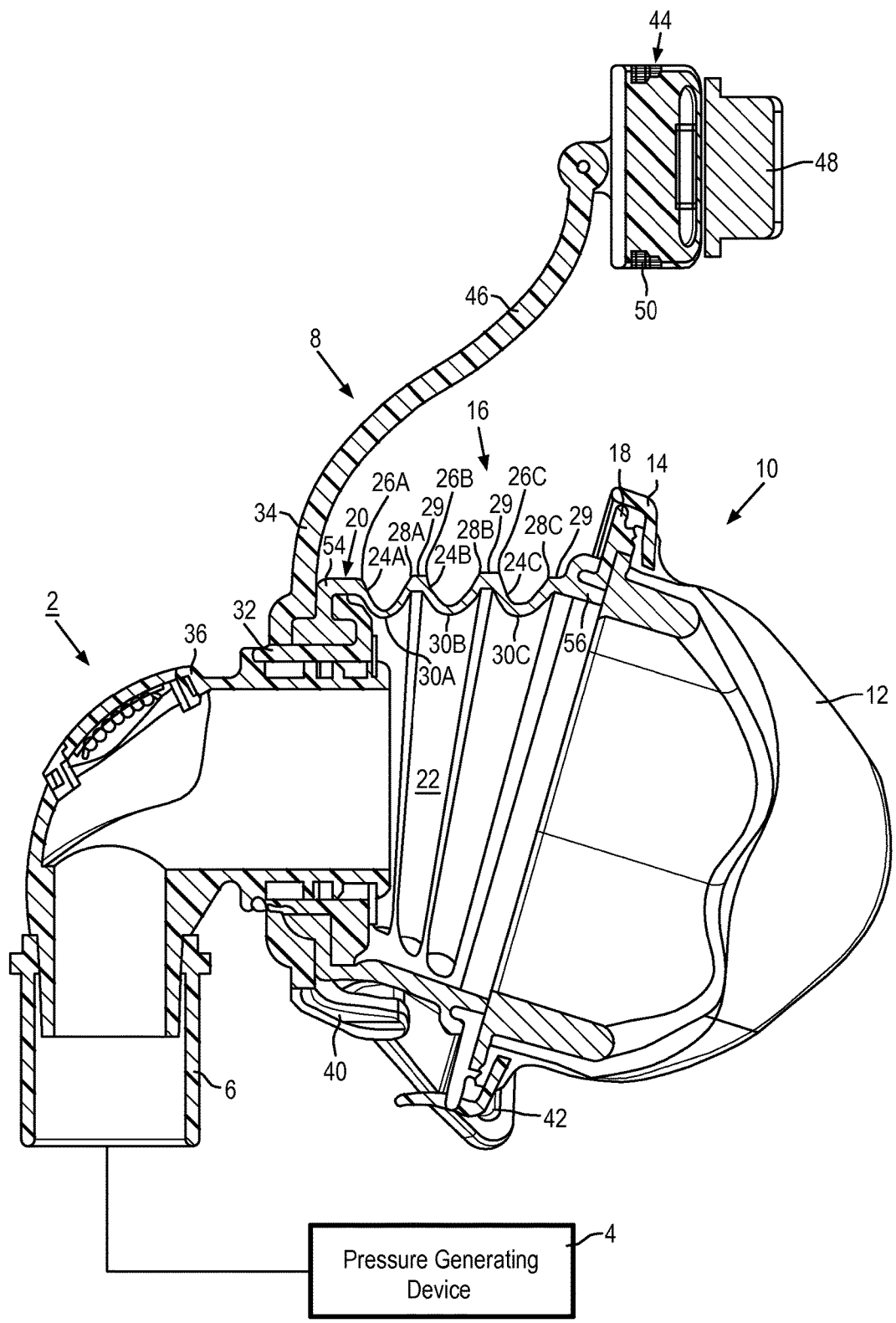
FIG. 2 is a schematic view of a system adapted to provide a regimen of respiratory therapy to a patient according to one exemplary embodiment of the present invention showing a side view, partially in section, of a patient interface device used in such a system.

FIG. 1 is a schematic/isometric view and FIG. 2 is a schematic/cross-sectional view of system 2 adapted to provide a regimen of respiratory therapy to a patient according to one exemplary embodiment of the present invention. System 2 includes a pressure generating device 4, a delivery conduit 6, and a patient interface device 8 (delivery conduit 6 and patient interface device 8 are together often referred to as a patient circuit). Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

Patient interface device 8 includes a patient sealing assembly, which in the illustrated embodiment is mask 10 in the form of a nasal mask. However, any type of patient sealing assembly, such as a nasal/oral mask, a nasal cushion, or a full face mask, which facilitates the delivery of the flow of breathing gas to the airway of a patient, may be substituted for mask 10 while remaining within the scope of the present invention.

Mask 10 includes a sealing cushion 12, which is coupled to a rigid frame 14. In the illustrated embodiment, sealing cushion 12 is defined from a unitary piece of soft, flexible, cushiony, elastomeric material, such as, without limitation, silicone, an appropriately soft thermoplastic elastomer, a closed cell foam, or any combination of such materials.

Mask 10 is fluidly coupled to an adjustment assembly generally indicated at 16. In the illustrated exemplary embodiment, adjustment assembly 16 includes a rigid frame 18 coupled to a grooved adjustment mechanism 20, described in greater detail below. The distal end of adjustment assembly 16 is coupled to a coupling frame 32, which in turn is coupled to a rigid support structure 34 forming part of patient interface device 8. In addition, support structure 34 is coupled to an elbow conduit 36 in a manner wherein adjustment assembly 16 and mask 10 are fluidly coupled to elbow conduit 36. Elbow conduit 36 is structured to be fluidly coupled to delivery conduit 6 which is in fluid communication with pressure generating device 4.

Support structure 34 includes a base portion 38 having a pair of extension members 40 extending from opposites side thereof. Each extension member 40 includes a headgear coupling mechanism 42 that engages a headgear strap (not shown) to patient interface device 8. In the illustrated embodiment, headgear coupling mechanism 42 is loop sized and configured to receive a respective lower headgear strap of a headgear assembly (also not shown) for securing patient interface device 8 to the head of the patient. It is to be understood that the present invention contemplates other structures for headgear coupling mechanism 42, such as snaps and ball-and-socket connections.

Patient interface device 8 further includes a forehead support 44 attached to an extension member 46 extending from a base portion 38. Forehead support 44 includes a forehead cushion 48 that is coupled to a support frame 50. Forehead support 44 is structured to provide additional support for patient interface device 8 by engaging the forehead of the patient. Support frame 50 includes headgear coupling mechanisms 52 provided at opposite ends thereof. In the illustrated embodiment, each headgear coupling mechanism 52 is in the form of a loop structured to receive a respective upper headgear strap of a headgear assembly (not shown) for securing patient interface device 8 to the head of the patient. As with headgear coupling mechanisms 42, the present invention contemplates other structures for headgear coupling mechanisms 52, such as snaps and ball-and-socket connections.

It is to be understood that the present invention contemplates other structures and configurations for forehead support 44 and the associated elements. For example, forehead support 44 can include an adjustment mechanism that allows the position of support frame 50 to be adjusted relative to support structure 34. Of course, support frame 50 and forehead cushion 48 can have other configurations as well.

Grooved adjustment mechanism 20 includes a main body 22 formed from an elastic material, such as, without limitation, silicone, a thermoplastic elastomer or another material with suitable elastomeric properties. In addition, main body 22 includes a plurality of grooves 24 (24A, 24B, 24C in the illustrated embodiment). As seen in FIG. 1, each individual groove 24 extends laterally along at least a portion of main body 22. In addition, as seen in FIGS. 1 and 2, the series of grooves 24 extends longitudinally along main body 22. In the illustrated embodiment, each groove 24 extends laterally along the lateral sides and top of main body 22 but not the bottom of main body 22, and thus the grooves 24 only partially surround main body 22. In addition, as seen in FIG. 2, each groove 24 has a first end 26, a second end 28 and a recessed hinge portion 30 located therebetween. Furthermore, adjacent grooves 24 are separated from one another by a transition region 29 of main body 22. Each groove 24 and its adjacent transition region 29 are referred to herein as a "convolution", and thus grooved adjustment mechanism 20 includes a plurality of convolutions (grooved adjustment mechanism 20 shown in FIGS. 1 and 2 includes three convolutions). In other words, grooved adjustment mechanism 20 is sinuous in shape and each convolution is a sinuosity.

According to an aspect of an embodiment of the present invention, grooved adjustment mechanism 20 functions as an elastomeric spring that has a specific compression range and controlled stiffness profile. In particular, in the exemplary embodiment, the stiffness of each groove 24, and thus each convolution, increases from the front end 54 of main body 22 (adjacent to coupling frame 32) to the rear end 56 of main body 22 (adjacent to frame 18). Thus, the force required to collapse each groove 24, and thus each convolution, similarly increases along main body 22 from front end 54 to rear end 56. In the illustrated embodiment, groove 24B is stiffer than groove 24A, and groove 24C is stiffer than groove 24B. As a result, the present invention achieve the beneficial result that when a force is applied to support structure 34 (e.g., as a result of tightening the headgear), groove 24A will collapse first (least force required), groove 24B will collapse next (next most force required), and groove 24C will collapse last (most force required). This results in a controlled increasing stiffness as grooved adjustment mechanism 20 collapses (each collapse of a convolution can be full or partial). This controlled increasing stiffness allows the user to tighten the patient interface device against his or her face and find a position or headgear tensioning force that is most comfortable for that particular user. Thus, a common patient interface device will provide this benefit over a wide variety of users having different facial shapes, sizes, geometries, etc.

In addition, in one particular, non-limiting embodiment, each groove 24A, 24B, 24C has a stiffness that is greater than the stiffness of the walls of cushion 12. In another embodiment, some portions of cushion 12 (e.g., the flap thereof) will collapse prior to groove 24A. In still another embodiment, the combined stiffness of grooves 24A, 24B, 24C is greater than the stiffness of the wall of cushion 12. In yet another embodiment, the stiffness of groove 24 A is set, tuned, and/or adjusted to collapse after an appropriate amount and/or portion of the cushion 12 collapses.

Figure 3:
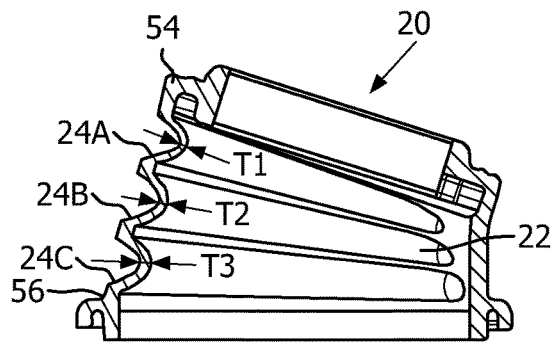
FIGS. 3-6 are a cross-sectional views of an exemplary embodiment of a grooved adjustment mechanism used in the patient interface device of the present invention.

In the illustrated embodiment, the specific stiffness of each groove 24 (and thus each convolution including the groove 24) is controlled and determined based on the cross-sectional thickness of the portion of main body 22 defining the groove 24. In particular, the stiffness of a groove 24 is directly related to the cross-sectional thickness of the portion of main body 22 defining the groove 24 (the greater the thickness, the greater the stiffness). Such cross-sectional thicknesses are illustrated in FIG. 3, which is a cross-sectional view of an exemplary embodiment of a grooved adjustment mechanism 20. As seen in FIG. 3, $T3>T2>T1$, wherein T3 is the cross-sectional thickness of the portion of main body 22 defining groove 24C, T2 is the cross-sectional thickness of the portion of main body 22 defining groove 24B, and T1 is the cross-sectional thickness of the portion of main body 22 defining groove 24 A.

Figure 4:
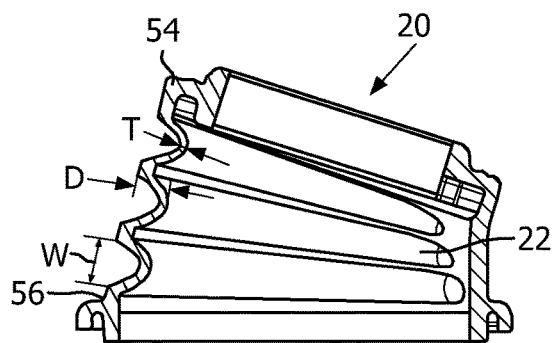

Furthermore, the stiffness of each groove 24 (and thus each convolution including the groove 24) may also be determined by other factors, including the depth D of each groove 24 (FIG. 4), the width W of each groove 24 (FIG. 4), the durometer of the material used to form main body 22, and the general geometry of each groove 24 (e.g., the shape and/or radius of curvature of the groove 24 or the radius of the transition between the ends 26 of each groove 24 and the associated transition regions 29).

In addition to determining stiffness, the width W also determines the amount of travel/displacement produced from the groove 24. Furthermore, the stiffness of each convolution may be controlled by controlling the cross-sectional thickness of the transition region 29 of the convolution. These factors may be controlled alone or in combination with one another and/or in combination with the groove thickness as described above to determine the stiffness of each convolution in a particular grooved adjustment mechanism 20. As a result, the stiffness profile of the particular grooved adjustment mechanism 20 may be controlled to obtain a desired pressure/force response and collapse profile.

Figure 5:
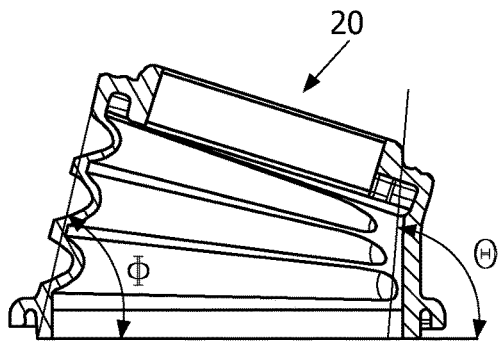
Figure 6:
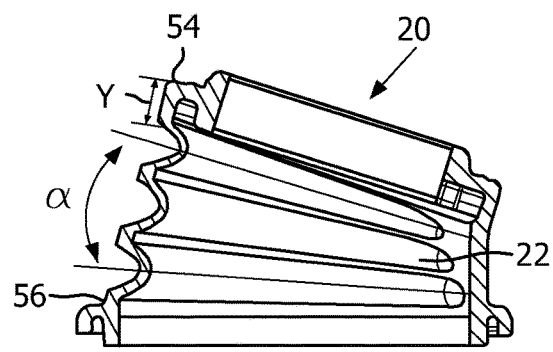

FIGS. 5 and 6 illustrate four other features/parameters of grooved adjustment mechanism 20 that may be controlled to determine the manner in which grooved adjustment mechanism 20 collapses in response to an applied force. Those features/parameters are: (i) the angle $\phi$ of the top wall of main body 22 with respect to the plane defining rear end 56 of main body 22 (FIG. 5), (ii) the angle $\theta$ of the bottom wall of main body 22 with respect to the plane defining rear end 56 of main body 22 (FIG. 5), (iii) the angle $\alpha$ between a line normal to the center of the front-most groove 24 on main body 22 and a line normal to the center of the rear-most groove 24 on main body 22 (each line divides the cross-section of the groove 24 in half) (FIG. 6), and (iv) the distance Y between the front edge of front end 54 of main body 22 and the first end 26 of the front-most groove 24 on main body 22. In addition, to the extent that the angle $\alpha$ is greater than zero, the grooved adjustment mechanism 20 will collapse in an arcuate fashion in response to an applied force.

Table 1 below provides particular values for the features/parameters of four particular, non-limiting embodiments of a grooved adjustment mechanism 20.

TABLE 1

| Embodiment | T1 (mm) | T2 (mm) | T3 (mm) | Φ (deg) | θ (deg) | α (deg) | Y (mm) |
|---|---|---|---|---|---|---|---|
| 1 | 0.89 | 1.14 | 1.31 | 81.2 | 71.5 | 12.1 | 4.6 |
| 2 | 0.89 | 1.14 | 1.40 | 75.3 | 90.0 | 12.0 | 3.9 |
| 3 | 0.89 | 1.14 | 1.40 | 77.2 | 74.1 | 9.8 | 6.3 |
| 4 | 0.90 | 1.15 | 1.40 | 77.9 | 87.4 | 8.5 | N/A |

Figure 7:
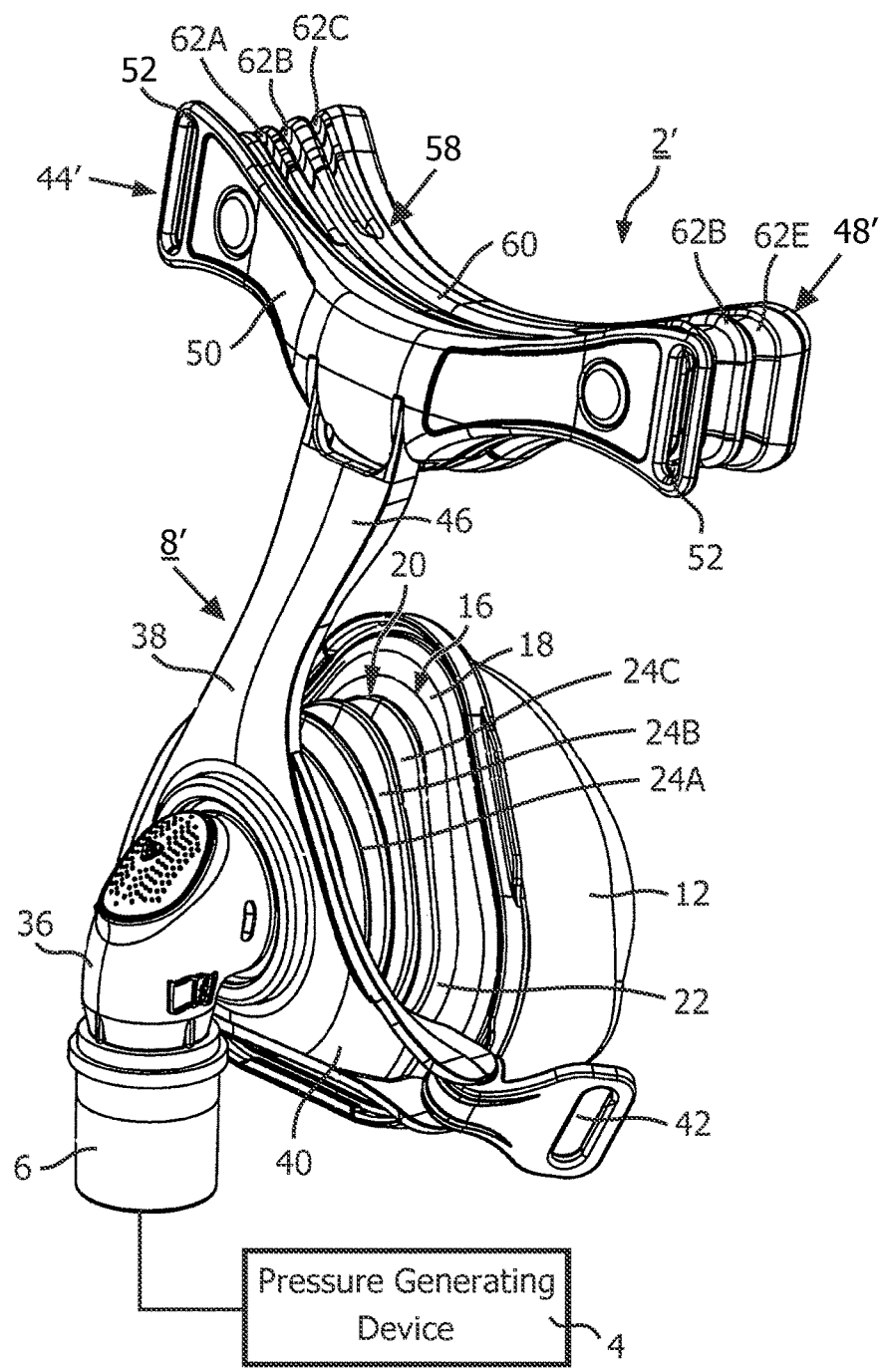
FIGS. 7 and 8 are front perspective and top perspective views, respectively, of a system adapted to provide a regimen of respiratory therapy to a patient showing an alternative exemplary embodiment for the patient interface device.
Figure 8:
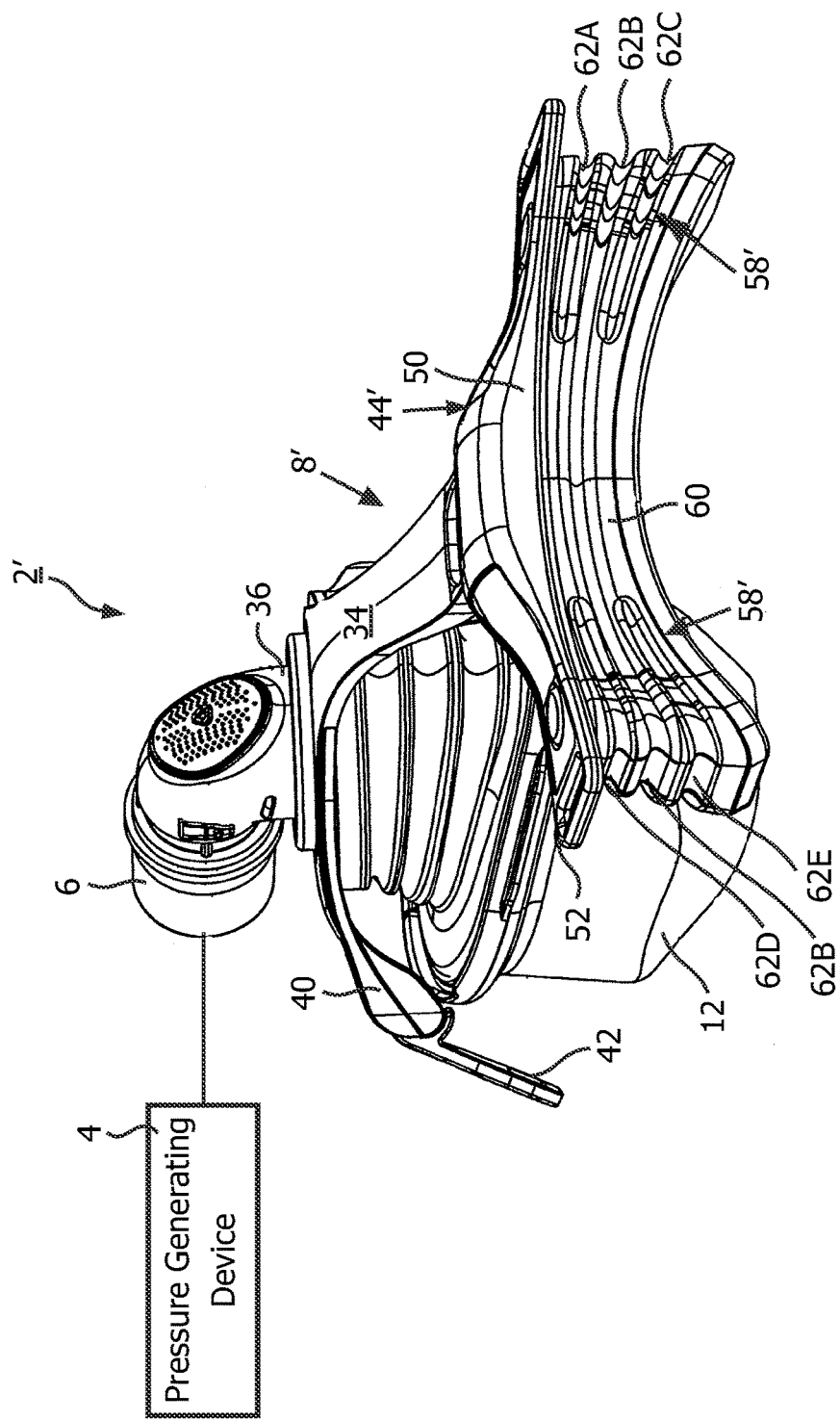
Figure 9:
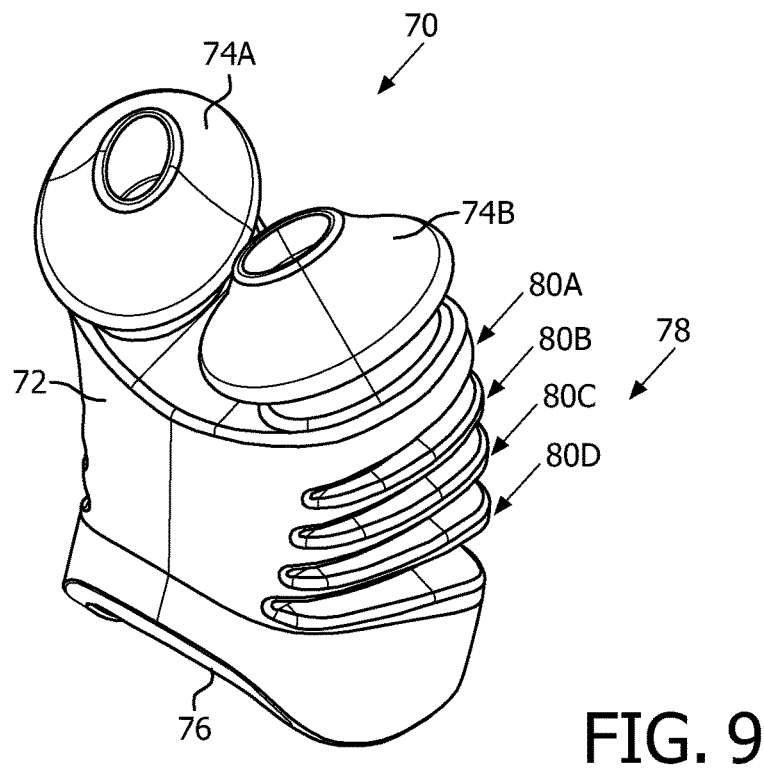
FIGS. 9, 10, 11, 12, and 13 are front perspective, front elevational, rear elevational, side elevational, and cross-sectional views, respectively, of a nasal cushion according to an alternative exemplary embodiment of the present invention.
Figure 10:
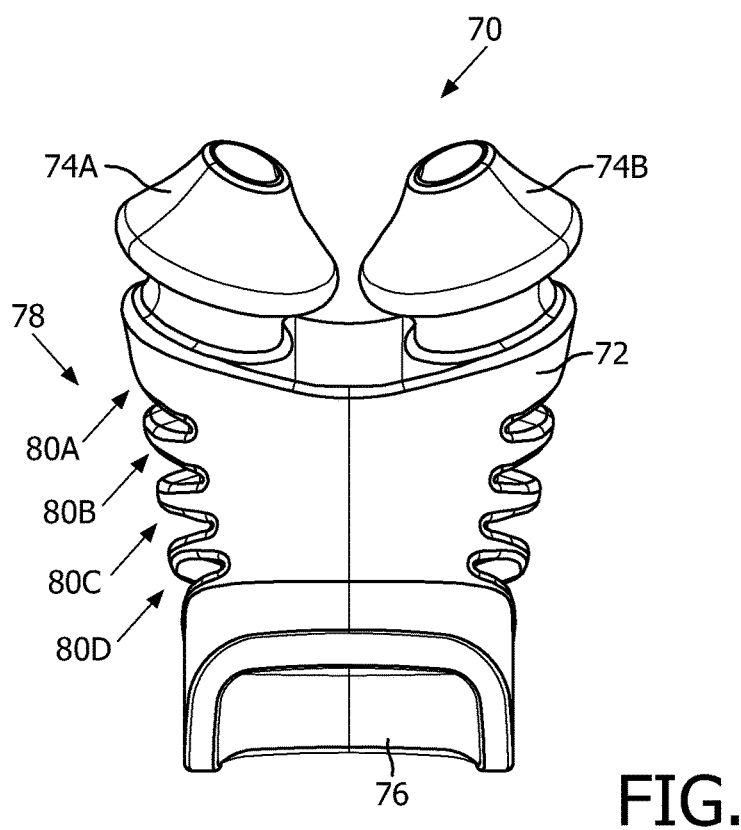
Figure 11:
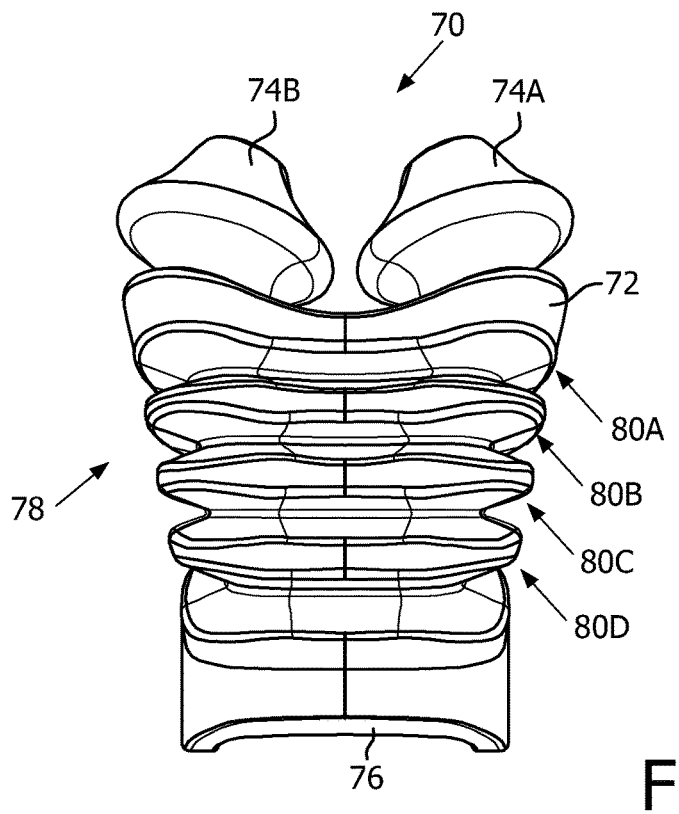

FIGS. 7 and 8 are front and top isometric views, respectively, of system 2' adapted to provide a regimen of respiratory therapy to a patient according to an alternative exemplary embodiment of the present invention. System 2' is similar to system 2 shown in FIGS. 1 and 2, and like components are labeled with like reference numerals. System 2', however, includes an alternative patient interface device 8' having an alternative forehead support 44'. The alternative forehead support 44' includes an alternative forehead pad 48' that includes grooved adjustment mechanism 58 that is similar to grooved adjustment mechanism 20. Grooved adjustment mechanism 58 includes main body 60 formed from an elastic material, such as, without limitation, silicone, a thermoplastic elastomer or another material with suitable elastomeric properties.

In addition, main body 60 includes a plurality of grooves 62 (and thus a plurality of convolutions) that are similar to grooves 24 described elsewhere herein. In the illustrated embodiment, main body 60 includes central groove 62B the extends around the entire periphery of main body 60, grooves 62A and 62C at a first lateral end of main body 60 that each extend along the top, side and bottom of that end (but not into the center of main body 60), and grooves 62D and 62E at a second (opposite) lateral end of main body 60 that each extend along the top, side and bottom of that end (but not into the center of main body 60). Like grooved adjustment mechanism 20, grooved adjustment mechanism 58 functions as an elastomeric spring that has a specific compression range and controlled stiffness profile. In the exemplary embodiment, the stiffness of each groove 62 (and thus each convolution including the groove 62) increases from the front to the back of forehead pad 48' (i.e., from support frame 50 to the patient contacting side of forehead pad 48'). Thus, the force required to collapse each groove 62 (and thus each convolution including the groove 24) similarly increases along main body 60.

In the illustrated embodiment, groove 62B is stiffer than grooves 62A and 62D, and grooves 62C and 62E are stiffer than groove 62B. As a result, when a force is applied to support frame 50, grooves 62A and 62D will collapse first (least force required), groove 62B will collapse next (next most force required), and grooves 62C and 62E will collapse last (most force required), the result being a controlled increasing stiffness as grooved adjustment mechanism 58 collapses. The stiffness of each groove 62 and each convolution may be selectively determined and controlled as described elsewhere herein in connection with grooves 24.

Thus, in the embodiment just described, grooved adjustment mechanism 58, unlike grooved adjustment mechanism 20, is provided outside the air flow path. It should be understood that grooved adjustment mechanisms may be provided in other portions of a patient interface devices that are outside the air flow path, such as, without limitation, in headgear adjustment components or mask articulation joints.

FIGS. 9, 10, 11, 12, and 13 are front perspective, front elevational, rear elevational, side elevational and cross-sectional views, respectively, of nasal cushion 70 according to an alternative exemplary embodiment of the present invention. As will be appreciated by those of skill in the art, nasal cushion 70 may be employed as part of the patient sealing assembly of a patent interface device (like cushion 12 in FIGS. 1 and 2) having among other components, a headgear assembly, as described in, for example and without limitation, United States patent Application Nos. 20080196727 and 20080245369, assigned to the assignee of the present invention and incorporated herein by reference.

Figure 12:
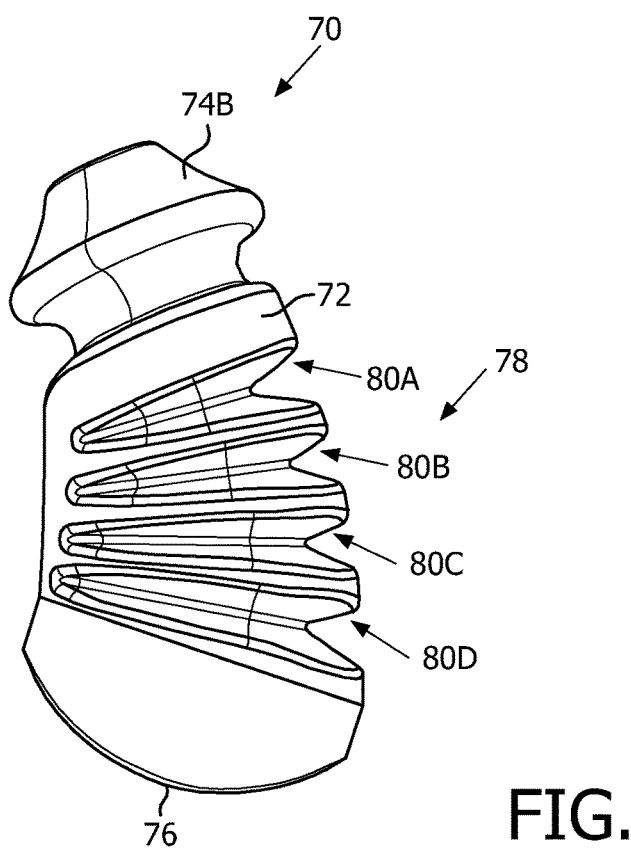
Figure 13:
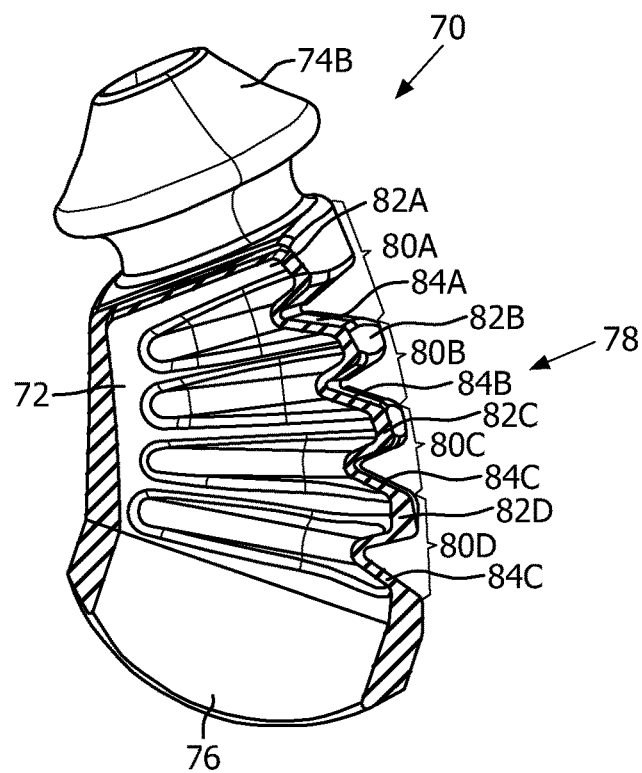
Figure 14:
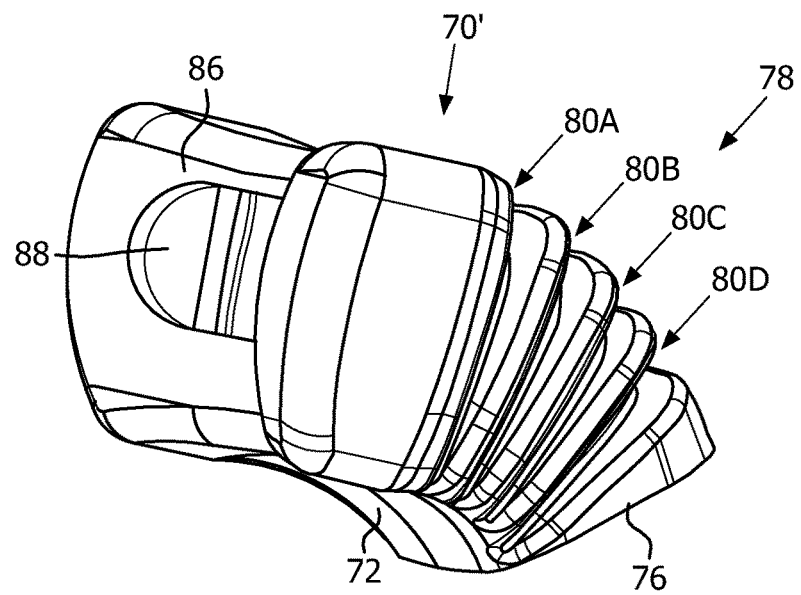
FIGS. 14, 15, 16, 17, and 18 are front perspective, front elevational, rear elevational, side elevational, and cross-sectional views, respectively, of a nasal cushion according to a further alternative exemplary embodiment of the present invention.
Figure 15:
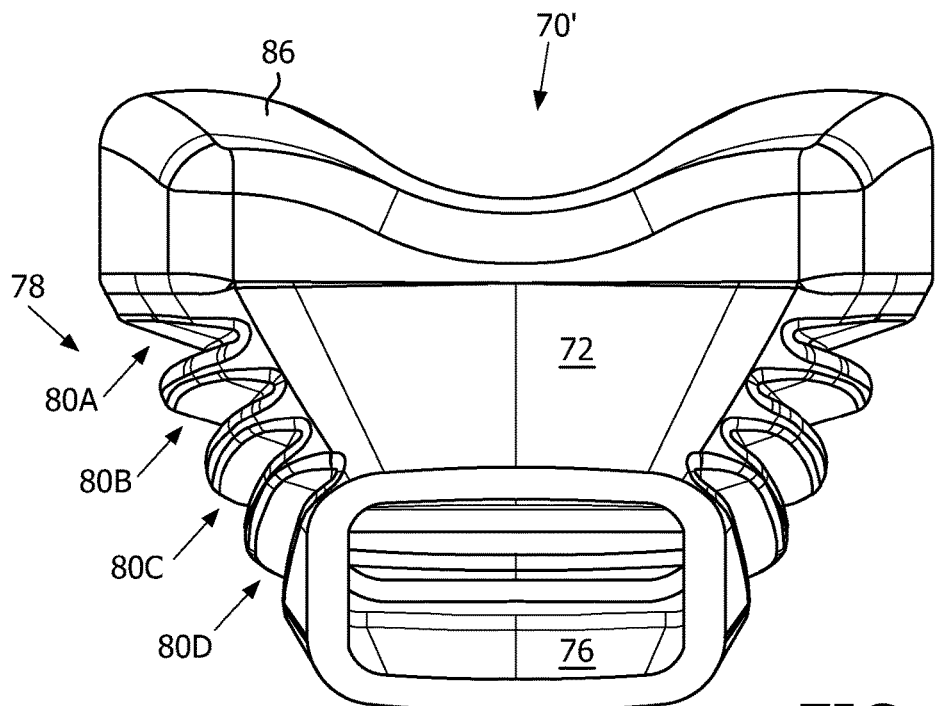
Figure 16:
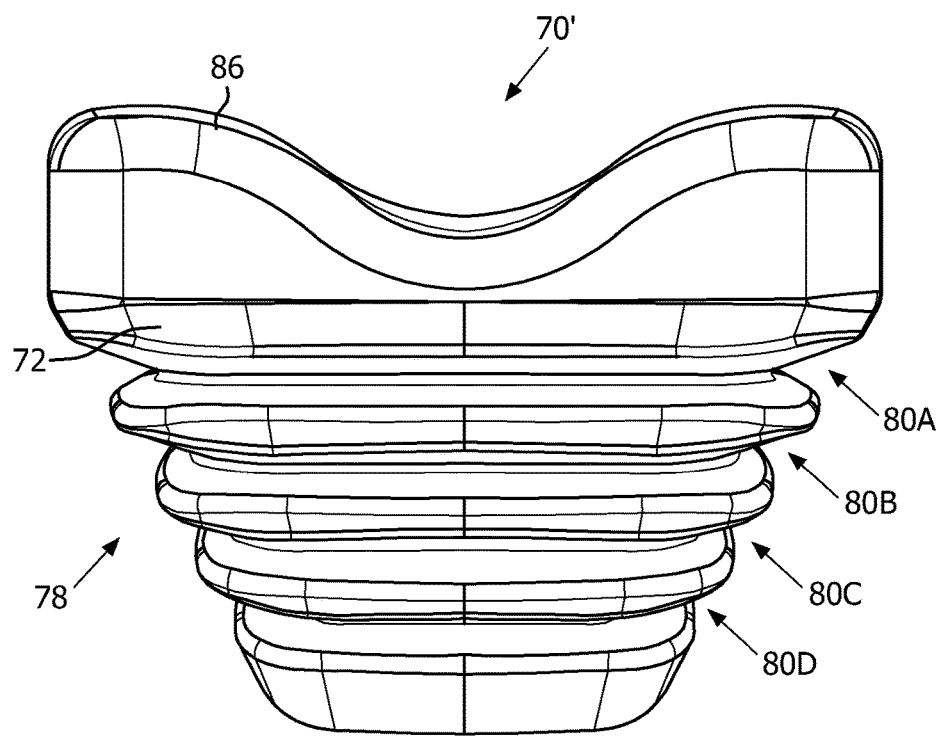
Figure 17:
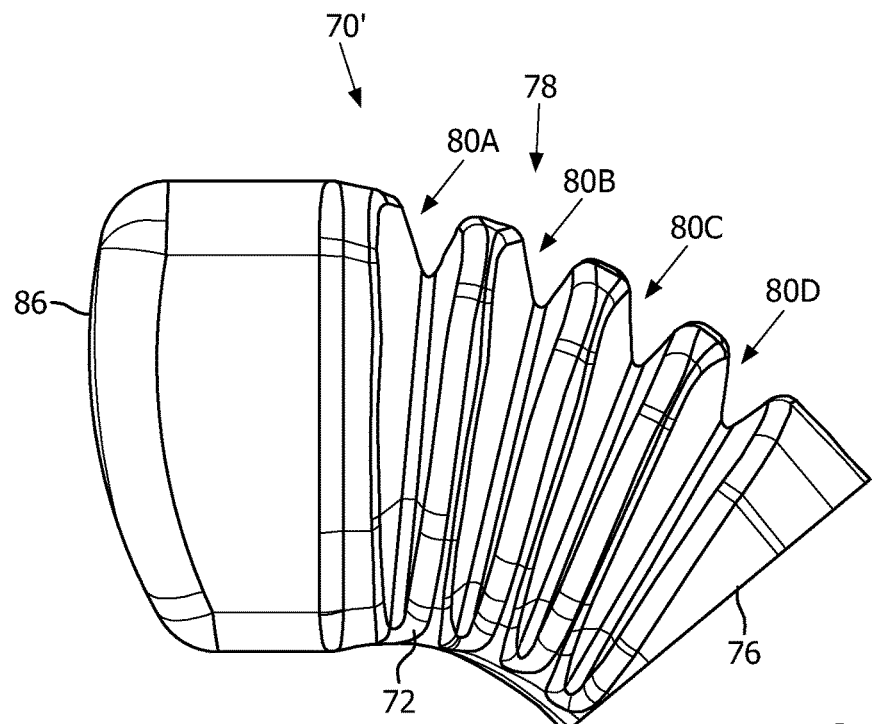
Figure 18:
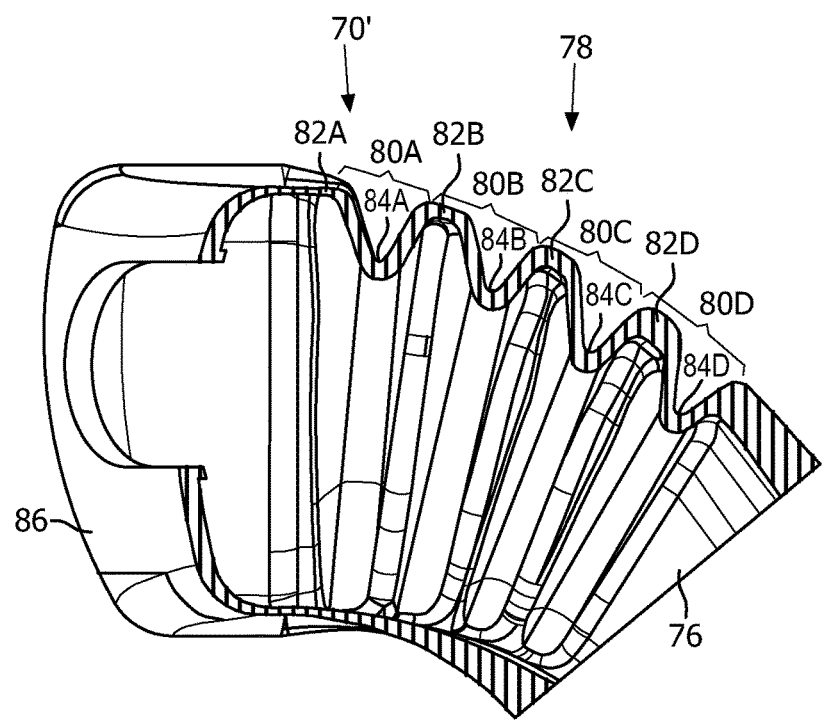

Nasal cushion 70 is formed from an elastic material, such as, without limitation, silicone, a thermoplastic elastomer or another material with suitable elastomeric properties, and includes main body 72, nasal prongs 74A and 74B provided at a first end of main body 72 and structured to engage the nares of the patient, and orifice 76 provided at a first end of main body 72 and structured to enable nasal cushion 70 to be in fluid communication with a delivery conduit and pressure generating device as described elsewhere herein. Nasal cushion 70 is commonly referred to as a "pillows" style cushion. As seen in FIG. 12, main body 72 has an arced contour and nasal prongs 74A and 74B have a forward cant, as opposed to being parallel to a line longitudinally bisecting main body 72.

Nasal cushion 70 includes grooved adjustment mechanism 78 that is similar to grooved adjustment mechanism 20. Grooved adjustment mechanism 78 is provided in main body 72 of nasal cushion 70. Grooved adjustment mechanism 78 includes a plurality of convolutions 80 each including a transition region 82 and a groove 84 (similar to grooves 24 described elsewhere herein). In the illustrated embodiment, grooved adjustment mechanism 78 includes convolutions 80A, 80B, 80C, 80D. Each individual convolution 80 extends laterally along at least a portion of main body 72. In addition, the series of convolutions 80 extends longitudinally along main body 72. In the illustrated embodiment, each convolution 80 extends laterally along the lateral sides and rear of main body 72 but not the front of main body 72, and thus the convolutions 80 only partially surround main body 72. As a result, the front side of main body 72 is more rigid than the rear and lateral sides of main body 72.

Like grooved adjustment mechanism 20, grooved adjustment mechanism 78 functions as an elastomeric spring that has a specific compression range and controlled stiffness profile. In the exemplary embodiment, the stiffness of each convolution 80 increases from the first end of main body 72 (adjacent nasal prongs 74A and 74B) to the second end of main body 72 (defining orifice 76). Thus, the force required to collapse each convolution 80 similarly increases along main body 72 from the first end to the second end. In the illustrated embodiment, convolution 80B is stiffer than convolution 80A, convolution 80C is stiffer than convolution 80B, and convolution 80D is stiffer than convolution 80C. As a result, when a force is applied to the first end of main body 72, convolution 80A will collapse first (least force required), convolution 80B will collapse next (next most force required), convolution 80C will collapse next (next most force required), and convolution 80D will collapse last (most force required), the result being a controlled increasing stiffness as grooved adjustment mechanism 78 collapses (each convolution may fully or partially collapse).

In the illustrated embodiment, the stiffness of each convolution 80 is determined by the cross-sectional thickness of the transition region 82 of the convolution 80 (the greater the thickness, the greater the stiffness). The stiffness of each convolution 80 may be selectively determined and controlled in a number of other ways, including, without limitation, the thickness of grooves 84, the width of transition regions 82 or grooves 84, the depth of grooves 84, the material durometer and/or the geometry of transition regions 82 and grooves 84.

FIGS. 14, 15, 16, 17, and 18 are front perspective, front elevational, rear elevational, side elevational and cross-sectional views, respectively, of nasal cushion 70' according to a further alternative exemplary embodiment of the present invention. Nasal cushion 70' is similar to nasal cushion 70 (like parts are labeled with like reference numerals), except that instead of nasal prongs 74A and 74B, nasal cushion 70' includes sealing surface 86 defining orifice 88 for sealing engagement with the patient's nose to deliver gas to the airway of the patient through the patient's nares. Nasal cushion 70' is commonly referred to as a "saddle" or "cradle" style cushion.

Nasal cushion 70 and nasal cushion 70' are intended to mount at the tip/base of the patient's nose with little flexibility. As noted elsewhere herein, nasolabial angles can vary widely among patients. The grooved adjustment mechanism 78 provided as part of each of nasal cushion 70 and nasal cushion 70' allows for the angle of nasal cushion 70 and nasal cushion 70' to be readily adjusted so that differing nasolabial angles can be accommodated while still providing adequate sealing and comfort. More specifically, in the exemplary embodiment, convolutions 80 of grooved adjustment mechanism 78 extend along only the lateral sides and rear of main body 72 and thus allow the position of the patient contacting/sealing surface(s) to be changed in an arcuate fashion to accommodate different nasolabial angles. In addition, in the exemplary embodiment, the front of main body 72 does not include any convolutions 80 and thus is more rigid to maintain a good seal at the nose tip.

Figure 19:
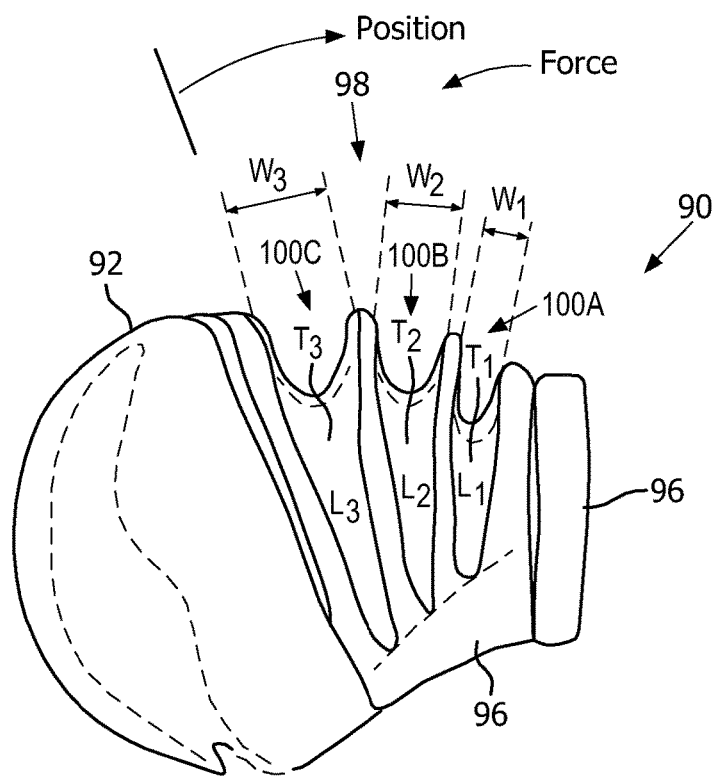
FIG. 19 is a side elevational view of a cushion according to a further alternative exemplary embodiment of the present invention.

FIG. 19 is a side elevational view of cushion 90 according to a further alternative exemplary embodiment of the present invention. As will be appreciated by those of skill in the art, cushion 90 may be employed as part of the patient sealing assembly of a patent interface device (like cushion 12 in FIGS. 1 and 2) having among other components, a headgear assembly, as described in, for example and without limitation, United States patent Application Nos. 20080196727 and 20080245369, assigned to the assignee of the present invention and incorporated herein by reference.

Cushion 90 is formed from an elastic material, such as, without limitation, silicone, a thermoplastic elastomer or another material with suitable elastomeric properties, and includes sealing portion 92 and adjustment portion 94. Sealing portion 92 and adjustment portion 94 may be molded as a single, integrated component, or may be molded separately from the same or different materials and coupled to one another. Sealing portion 92 is structured to engage the face of the patient (e.g., covering the nose or nose and mouth of the patient). Adjustment portion 94 includes orifice 96 structured to enable cushion 90 to be in fluid communication with a delivery conduit and pressure generating device as described elsewhere herein.

Adjustment portion 94 of cushion 90 includes grooved adjustment mechanism 98. Grooved adjustment mechanism 98 includes a plurality of convolutions each including a groove 100. In the illustrated embodiment, grooved adjustment mechanism 98 includes three convolutions having grooves 100A, 100B, 100C. It should be understood that three convolutions is meant to be exemplary only, and that two or four or more convolutions may also be employed. Each individual groove 100 extends laterally along at least a portion of adjustment portion 94. In addition, the series of convolutions and grooves 100 extends longitudinally along adjustment portion 94. In the illustrated embodiment, each groove 100 extends laterally along the lateral sides and top of adjustment portion 94 but not the bottom of adjustment portion 94, and thus the grooves 100 only partially surround adjustment portion 94. As a result, the top side of adjustment portion 94 is less rigid than the bottom side of adjustment portion 94.

Grooved adjustment mechanism 98 functions as an elastomeric spring that has a specific compression range and controlled stiffness profile. In addition, as shown in FIG. 19, groove 100A has a width ($W_1$), a thickness ($T_1$) (cross-sectional thickness measured as described elsewhere herein) and a length ($L_1$), groove 100B has a width ($W_2$), a thickness ($T_2$) (cross-sectional thickness measured as described elsewhere herein) and a length ($L_2$), and groove 100C has a width ($W_3$), a thickness ($T_3$) (cross-sectional thickness measured as described elsewhere herein) and a length ($L_3$). In the illustrated embodiment, $W_1$, $W_2$ and $W_3$ are each different from one another, $T_1$, $T_2$ and $T_3$ are each different from one another, and $L_1$, $L_2$ and $L_3$ are each different from one another. In one particular, non-limiting embodiment, also illustrated in FIG. 19, $W_1 < W_2 < W_3$, $T_1 < T_2 < T_3$, and $L_1 < L_2 < L_3$. As a result of such dimensions, in the illustrated embodiment, the stiffness of each groove 100 increases from the first end of adjustment portion 94 adjacent sealing portion 92 to the second end of adjustment portion 94 adjacent orifice 96. Thus, the force required to collapse each convolution similarly increases along adjustment portion 94 from the first end to the second end, and the convolutions will collapse in that order in response to a force applied to the second end of adjustment portion 94.

Figure 20:
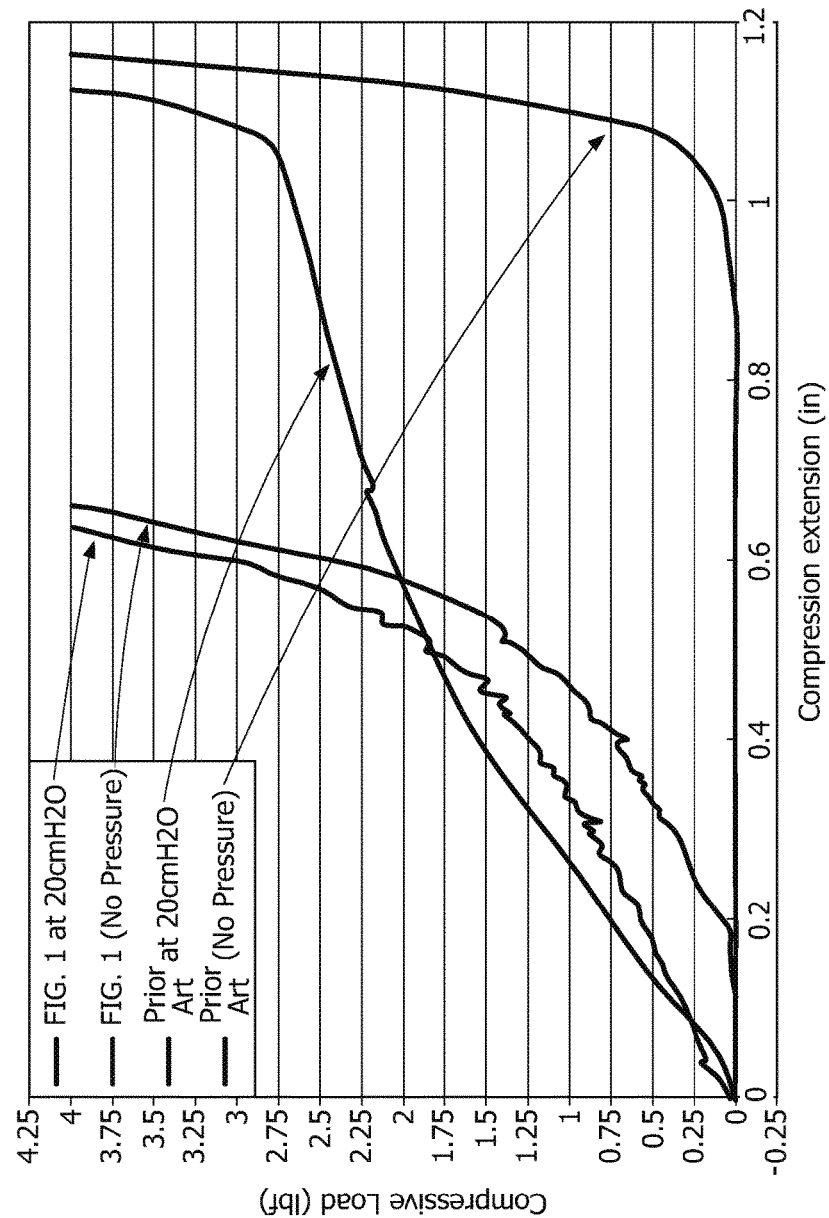
FIG. 20 is a graph demonstrating the performance of the embodiment of FIG. 1.

Finally, the present inventors conducted testing of the embodiment shown in FIG. 1 as compared to a typical conventional mask that has a single bellow in the cushion wall and a substantially even wall thickness and that does not include a grooved adjustment mechanism as described herein. The results of that testing are shown in the graph of compressive load v. compressive extension in FIG. 20. As shown in FIG. 20, the embodiment shown in FIG. 1 demonstrated increasing stiffness as the cushion is compressed along generally regular curves. By providing a predictable compressive load v. compressive extension curve, the grooved adjustment mechanism of the present invention has the advantage in the user and readily and repeatedly find the compressive load (headgear tension) that maximizes both comfort and sealing performance.

It can thus be appreciated that the present invention provides a patient interface device and mechanism for adjusting the position (e.g., angular position) of and/or the pressure exerted by a component of the patient interface device, such as a sealing cushion and/or support cushion, such as forehead cushion. It does so in a manner that maximizes both comfort and sealing performance in a repeatable fashion even over a wide range of different patients.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device for delivering a flow of breathing gas to an airway of a patient, comprising:
   a grooved adjustment mechanism having a main body formed from an elastic material, the main body having an outer surface having a plurality of convolutions provided therein and extending adjacent one another longitudinally along a side of the main body, each convolution including a groove, wherein each convolution has a stiffness associated therewith thereby forming a plurality of controlled stiffnesses from a first side of the main body to a second side of the main body with each of the controlled stiffnesses being associated with a respective one of the convulsions, wherein the controlled stiffnesses increase from the first side of the main body to the second side of the main body;
   a flexible sealing cushion;
   a rigid support structure; and
   an adjustment assembly provided between the sealing cushion and the support structure, wherein the adjustment assembly includes the grooved adjustment mechanism, and wherein the first side of the main body is adjacent and coupled to the rigid support structure and the second side of the main body is adjacent and coupled to the sealing cushion.

2. The patient interface device according to claim 1, wherein the controlled stiffness associated with each convolution is a groove stiffness of the groove of the convolution.

3. The patient interface device according to claim 2, wherein each groove is defined by a portion of the main body having an associated cross-sectional thickness, wherein the groove stiffness of each groove is determined by the cross-sectional thickness of the portion defining the groove, and wherein the cross-sectional thicknesses increase from the first side of the main body to the second side of the main body.

4. The patient interface device according to claim 2, wherein the groove stiffness of each groove is determined by at least one of a cross-sectional thickness of the groove, a depth the groove, a width of the groove and a geometry of the groove.

5. The patient interface device according to claim 1, wherein an angle α between a first line normal to a center of a front-most groove on the main body and a second line normal to a center of a rear-most groove on the main body is greater than zero.

6. The patient interface device according to claim 5, wherein the angle α is between 8 and 13 degrees.

7. The patient interface device according to claim 1, wherein the convolutions are provided on only a top side and each lateral side of the main body, wherein the top side is structured to face toward the eyes of the patient when the patient interface device is donned by the patient.

8. The patient interface device according to claim 1, wherein the rigid support structure includes a forehead support that includes a forehead cushion coupled to a support frame, and wherein the forehead cushion includes a second grooved adjustment mechanism having a second main body formed from an elastic material, the second main body having a second outer surface having a plurality of second convolutions provided therein and extending adjacent one another longitudinally along a side of the second main body, each second convolution including a groove.

9. The patient interface device according to claim 8, wherein the grooved adjustment mechanism is structured to collapse in an arcuate fashion in response to a force being applied to the grooved adjustment mechanism.

* * * * *